United States Patent
Ward, Jr.

(10) Patent No.: US 6,635,032 B2
(45) Date of Patent: Oct. 21, 2003

(54) PASSIVELY ACTIVATED SAFETY NEEDLE

(75) Inventor: William Edward Ward, Jr., Sumter, SC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/137,299

(22) Filed: May 3, 2002

(65) Prior Publication Data

US 2002/0165498 A1 Nov. 7, 2002

Related U.S. Application Data (60) Provisional application No. 60/288,757, filed on May 4, 2001.

(51) Int. Cl.$^7$ .................................................. A61M 5/32
(52) U.S. Cl. ........................ 604/192; 604/198; 128/919
(58) Field of Search ................................. 604/110, 117, 604/160, 161, 187, 192, 197, 198, 264, 263; 128/919; 206/363–366

(56) References Cited

U.S. PATENT DOCUMENTS 4,950,250 A    8/1990  Haber et al.
5,348,544 A  * 9/1994  Sweeney et al. ............ 604/192
5,584,818 A  * 12/1996 Morrison .................... 604/110
5,814,018 A  * 9/1998  Elson et al. ................ 604/110

FOREIGN PATENT DOCUMENTS

EP           0 838 227 A2    4/1998

* cited by examiner

*Primary Examiner*—Brian L. Casler
*Assistant Examiner*—Michael M. Thompson
(74) *Attorney, Agent, or Firm*—Hoffmann & Baron, LLP (57) ABSTRACT

A passively activated safety needle assembly includes a needle assembly, a shield assembly and a safety cap. The needle assembly includes a hub and a needle cannula that projects from the hub. The shield assembly includes a safety shield that is mounting for sliding movement along the needle cannula. The shield assembly also includes a plurality of arms articulated to one another to permit sliding movement of the safety shield along the needle cannula from a proximal position to a distal position where the tip of the needle cannula is shielded. A spring is mounted to the shield assembly and is operative to drive the safety shield from its proximal position to its distal position. The safety cap is mounted over shield assembly and holds the shield assembly in the proximal position. The arms are held during usage of the safety needle. Upon release of the arms, the spring automatically drives the shield distally without any user activation.

11 Claims, 7 Drawing Sheets

PASSIVELY ACTIVATED SAFETY NEEDLE

This application claims the benefit of U.S. Provisional Application No. 60/288,751, filed on May 4, 2001.

BACKGROUND OF THE INVENTION

1. Field of the Invention

The subject invention relates to a passively activated safety needle assembly to prevent accidental needle sticks.

2. Description of the Related Art

Many medical procedures require the use of a sharply pointed metallic needle cannula for obtaining a sample of fluid from a patient or for delivering a fluid to the patient. The sharply pointed metallic needle cannula must be handled carefully to avoid an accidental stick with the point of the needle cannula. An accidental stick with a sterile needle cannula is painful and can leave an open wound that is subject to infection. An accidental needle stick with a used needle cannula can transmit disease.

Safety shields are employed widely in the health care industry to eliminate or reduce the risk of accidental needle sticks. Safety shields have taken many forms, including shields that telescope along the needle cannula from a proximal position to a distal position. The distal tip of the needle cannula is exposed for use when the shield is in the proximal position. However, the pointed tip of the needle cannula is covered when the shield is in the distal position.

Some shields are large and telescope over a syringe, needle holder or other medical implement. Some such large shields also include coil springs to propel the shield distally. The spring typically is locked in a collapsed condition around proximal portions of the medical implement when the shield is retained in the proximal position. An actuator is triggered after use of the medical implement to release the spring and drive the shield distally into a shielding disposition around the needle cannula.

Other shields are much smaller and are configured to telescope only along the needle cannula. The shield in these prior art devices may be connected to the syringe or the needle hub by a tether or a linked array of hinged arms to limit the range of movement of the shield relative to the needle cannula. Thus, the shield can be moved distally into surrounding relationship with the tip of the needle cannula. However, the tether or hinged arms prevent the shield from sliding completely off the needle cannula. Some shield assemblies of this general type include a spring mechanism for assisting a portion of the distal movement of the shield along the needle cannula. A shielding assembly of this general type is shown in U.S. Pat. No. 5,348,544 which is assigned to the assignee of the subject invention. The shielding assembly shown in U.S. Pat. No. 5,348,544 requires the user to initiate shielding by exerting digital pressure on one of the hingedly connected arms. This initial digital pressure will be resisted by the spring. However, after a certain range of movement, the hingedly connected arms will be positioned such that the spring assists the distal movement of the shield. The needle shielding device shown in U.S. Pat. No. 5,348,544 is very effective. However, a device with passive or automatic shield actuation could provide certain advantages over the prior art.

SUMMARY OF THE INVENTION

The subject invention is directed to a passively activated safety needle assembly with a shield configured for sliding movement along a needle cannula. The needle cannula comprises a proximal end and a distal end that is sufficiently pointed for penetrating skin and adjacent tissue of a patient. The proximal end of the needle cannula may be mounted in a hub. The hub may be molded from plastic and may be configured for mounting to a syringe, a needle holder or other medical implement.

The shield of the passively activated safety needle assembly may be slidably movable along the needle cannula from a proximal position substantially adjacent the hub to a distal position for shielding the tip of the needle cannula. The needle shield may include a spring latch formed from a metallic material and biased against a lateral side of the needle cannula as the shield moves from the proximal position toward the distal position. The spring latch may be dimensioned and configured to overlie the distal tip of the needle cannula when the shield reaches its distal position.

The passively activated safety needle assembly of the subject invention further comprises connection means for limiting movement of the shield along the needle cannula. The connection means may comprise a flexible tether or a plurality of hingedly articulating arms that can move from a collapsed condition to an extended condition. The connection means is in the collapsed condition when the shield is in its proximal position relative to the needle cannula. However, the connection means is in a fully extended condition when the shield has advanced into shielding disposition around the tip of the needle cannula.

The connection means may comprise a distal end that is articulated to the shield and a proximal end that is articulated to or near the needle hub. More particularly, the proximal end of the connection means may be articulated directly to the needle hub. Alternatively, the proximal end of the connection means may be articulated to a base which in turn is connected securely to the needle hub.

The passively activated safety needle assembly of the subject invention further comprises a biasing means for urging the shield from the proximal position to the distal position. The biasing means may comprise a torsion spring mounted between a plurality of hingedly connected arms of the connection means. Alternatively, the biasing means may comprise a coil spring that surrounds the needle cannula at locations between the shield and the needle hub. The biasing means is disposed and configured for having stored energy when the safety shield is in its proximal position. Additionally, the biasing means is configured relative to the shield and the connection means such that the stored energy will urge the shield distally at all points along the range of movement of the shield. Thus, the biasing means is configured and disposed for urging the shield distally even when the shield is in its extreme proximal position. Accordingly, the biasing means avoids the need to initially exert digital pressure on the shield or on a hinged arm to start the shield moving toward the distal shielding position.

The passively activated needle assembly of the subject invention further comprises a safety cap that is removably engaged over the needle cannula prior to use. The safety cap may be formed from a rigid plastic material and may be dimensioned to cover the entirety of the needle cannula from the distal end to the proximal end. Proximal portions of the safety cap may be dimensioned for removable frictional engagement over the needle hub and/or over any base that may be provided to mount the connection means on the hub. A notch or slot may extend distally from the proximal end of the safety cap a sufficient distance for receiving the hingedly connected arms or other such connection means. The safety cap performs two functions. First, the safety cap prevents accidental sticks with the needle cannula prior to use. Additionally, the safety cap releasably holds the safety shield in a proximal position.

The shield of the subject invention initially is in its proximal position on the needle cannula with the connecting means in the collapsed condition and with the stored energy in the biasing means. The safety cap then is mounted over the needle cannula and over the shield sufficiently for removable frictional engagement of the safety cap with either the needle hub or with the base to which the connection means is articulated. This initial positioning of the safety shield and the safety cap is carried out at the place of manufacture and does not require any action by the health care worker.

A health care worker may mount the passively activated safety needle assembly to a syringe, needle holder or other medical implement in a conventional manner. This mounting may involve the mere axially movement of a Luer tip into a Luer receptacle of the needle hub. Alternatively, the needle hub of the passively activated safety needle can be threaded into engagement with a Luer collar.

The health care worker then grips the connection means and the syringe or needle holder between a thumb and forefinger. This engagement ensures that the shield will remain in a proximal position. The health care worker then grabs the safety cap with the other hand and pulls sufficiently to disengage the safety cap. The required pulling force is approximately the same as the pulling force to separate any safety cap from a needle assembly in the prior art. The health care worker then continues to exert digital pressure on the connection means and urges the exposed distal tip of the needle cannula into a targeted location on the patient for obtaining a fluid sample or for delivering a fluid drug to the patient. After the needle cannula has been placed in communication with the patient, the health care worker may release the grip on the connection means. This release of the connection means enables the spring to drive the safety shield distally. The distal movement of the safety shield along the needle cannula terminates when the distal end of the safety shield contacts the skin of the patient.

The needle cannula is removed from the patient after an appropriate volume of liquid has been withdrawn or after an appropriate dosage of a drug has been administered. Proximal movement of the needle cannula associated with the withdrawal of the needle cannula from the patient permits the safety shield to be driven further in a distal direction by the biasing means. Thus, the distal end of the safety shield will remain in contact with the skin of the patient as the needle is moved proximally relative to the patient. Upon complete removal of the needle cannula from the patient, the biasing means will advance the shield into its full shielding condition around the distal tip of the needle cannula. The safely shielded needle then can be separated from the syringe or needle holder and discarded into an appropriate sharps receptacle. Alternatively, the entire needle assembly and needle holder may be discarded.

The health care facility occasionally is a hectic environment, and fluids near the patient may make medical implements slippery. Thus, the potential exists for the health care worker to drop the needle assembly before use. Inadvertent dropping of the passively activated safety needle will immediately cause the shield to be propelled by the spring into its distal shielding position around the needle cannula. Hence, accidental sticks are avoided even in situations where the unused needle cannula is accidentally dropped.

DETAILED DESCRIPTION

Figure 1:
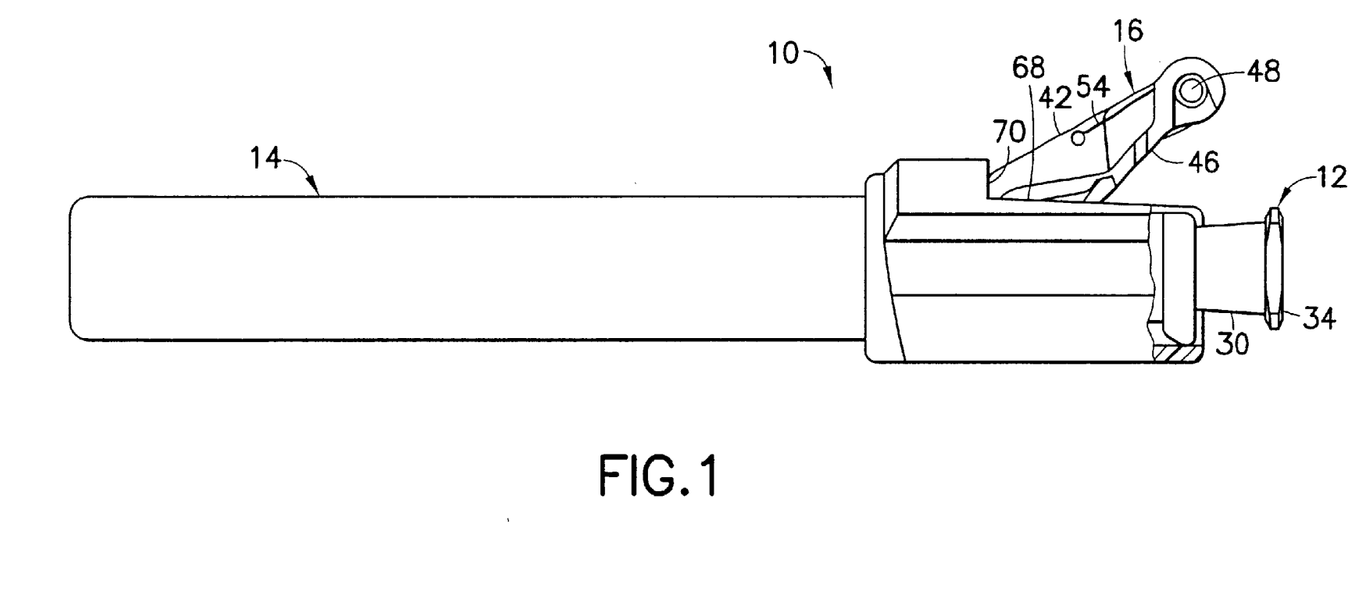
FIG. 1 is a side elevational view of a passively activated safety needle assembly in accordance with the subject invention.
Figure 2:
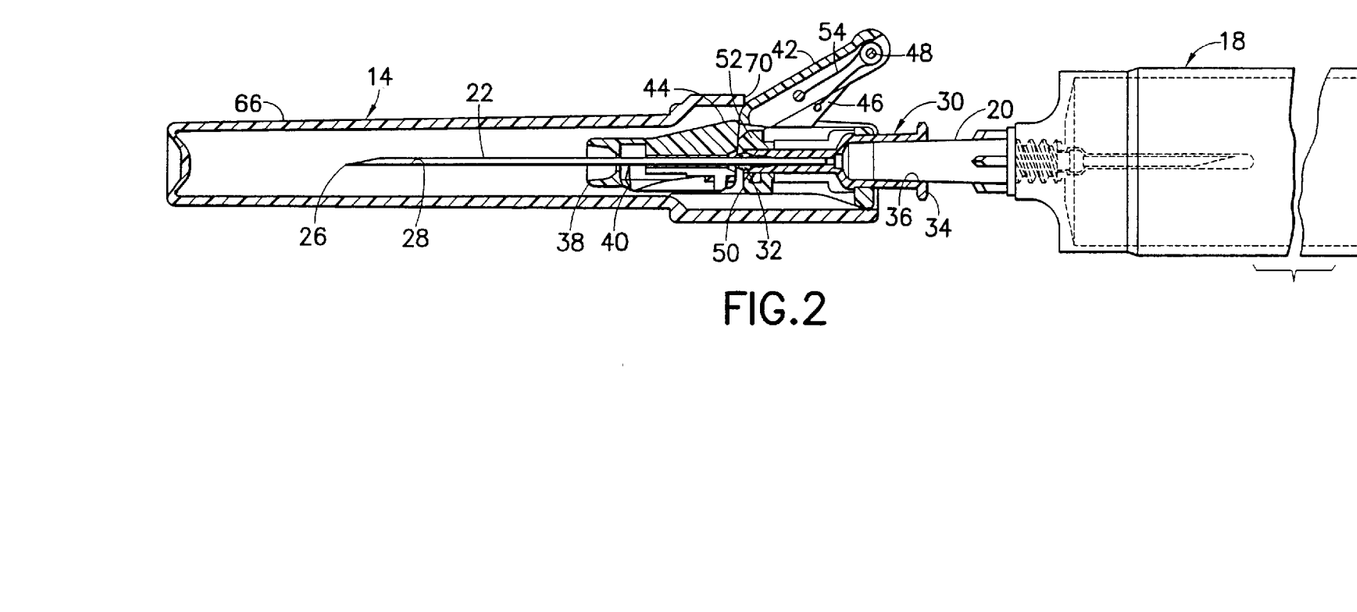
FIG. 2 is a longitudinal cross-sectional view of the passively activated safety needle assembly mounted to a needle holder.

A passively activated safety needle in accordance with the subject invention is identified generally by the numeral 10 in FIG. 1. Passively activated safety needle assembly 10 comprises a needle assembly 12, a safety cap 14 and a shield assembly 16. Safety needle assembly 10 can be mounted to a medical implement, such as a syringe or a needle holder. For example, FIG. 2 shows passively activated safety needle assembly 10 mounted to a needle holder 18 that is intended for use with evacuated blood collection tubes to collect samples of a patient's blood. Needle holder 18 may be of prior art design and is formed with a Luer tip 20 that has a passage therethrough.

Needle assembly 12 includes a needle cannula 22 with a proximal end 24, a distal end 26 that is beveled to a sharp tip and a lumen 28 extending between ends 24 and 26. Needle assembly 12 further includes a plastic hub 30. Proximal end 24 of needle cannula 22 is secured in hub 30 by adhesive 32. Hub 30 includes a proximal end 34 with a recess 36 configured for mounting over Luer tip 20 of needle holder 18 or over a Luer tip on another medical implement with which passively activated safety needle assembly 10 is employed. Thus, hub 30 permits communication between lumen 28 of needle cannula 22 and the passage through Luer tip 20 of needle holder 18.

Figure 4:
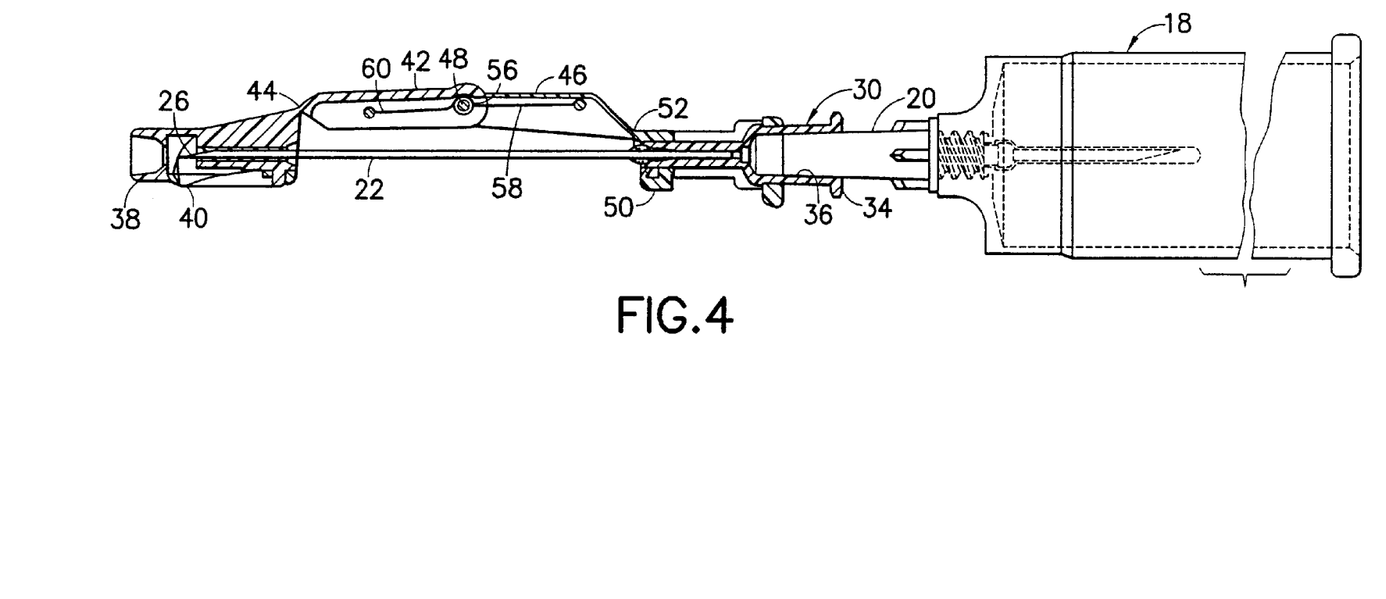
FIG. 4 is a cross-sectional view similar to FIGS. 2 and 3 after removal of the needle cannula from the patient and showing the shield in its fully extended condition.

Passively activated safety needle assembly 10 comprises a safety shield 38 slidably mounted over needle cannula 22 for movement from a proximal position adjacent hub 30 to a distal position where safety shield 38 surrounds distal end 26 of needle cannula 22. Safety shield 38 also is provided with a safety latch 40 formed from a metallic material. Latch 40 is biased against a side of needle cannula 32 when safety shield 38 is in the proximal position shown in FIG. 2. Latch 40 then slides against the side of needle cannula 22 as safety shield 38 is advanced from the proximal position shown in FIG. 2 toward the distal position shown in FIG. 4. When safety shield 38 reaches the distal position shown in FIG. 4, safety latch 40 will pass distal tip 26 of needle cannula 22. The inherent biasing forces of safety latch 40 will urge safety latch 40 over distal tip 26 of needle cannula 22 to prevent re-exposure of needle cannula 22.

Shield assembly 16 further includes a distal arm 42 that is connected unitarily to safety shield 38 by a first living hinge 44 that permits hinged movement between distal arm 42 and safety shield 38. A proximal arm 46 is hingedly connected to distal arm 42 by a hinge pin 48. Proximal arm 46 is connected unitarily to a safety shield base 50 by a second living hinge 52. Base 50 of shield assembly 16 is a generally tubular structure that is locked securely over hub 30 of needle assembly 12 in a manner that prevents removal without destruction of the respective components.

Shield assembly 16 further includes a torsion spring 54 with a coil 56, a proximal leg 58 and a distal leg 60. Coil 56 of torsion spring 54 is mounted over hinge pin 48 such that torsion spring 54 is effectively captured on shield assembly 16. Proximal leg 58 of torsion spring 54 is engaged with proximal arm 46 of shield assembly 16. Distal leg 60 of torsion spring 54 is engaged with distal arm 42 of shield assembly 16.

Arms 42 and 46 of shield assembly 16 are dimensioned and configured to permit safety shield 38 to be moved into the proximal position shown in FIG. 2, such that safety shield 38 abuts needle hub 30. Additionally, arms 42 and 46 of shield assembly 16 are dimensioned to permit safety shield 38 to be slid distally along needle cannula 22 and into a position where latch 40 snaps into engagement over distal end 26 of needle cannula 22. Torsion spring 54 is biased into a collapsed condition when safety shield 38 is in its proximal position along needle cannula 22 and substantially adjacent needle hub 30. Biasing forces of torsion spring 54 urge spring legs 58 and 60 away from one another, and thereby tend to urge arms 42 and 46 about hinge pin 48 and into an expanded condition. Thus, torsion spring 54 propels safety shield 38 distally along needle cannula 22. These forces of torsion spring 54 exist when safety shield 52 is in the proximal position shown in FIG. 2. Hence, there is no need to provide digital assistance through the first part of movement of safety shield 38, as had existed in the prior art.

Safety cap 14 of passively activated safety needle assembly 10 is molded unitarily from a rigid plastic material and includes an open proximal end 62, a closed distal end 64 and a rigid closed sidewall 66 extending between ends 62 and 64. Portions of tubular sidewall 66 adjacent distal end 62 are formed with a notch 68 that is dimensioned to slidably receive arms 42 and 46 when safety shield 38 is in the proximal position of FIG. 2. More particularly, notch 68 includes a distal end edge 70 that will abut against and lie partly over distal arm 42 of shield assembly 16. Simultaneously, portions of safety cap 14 adjacent proximal end 62 snap into engagement with base 50 of shield assembly 16. Thus, safety cap 14 is retained releasably over both needle assembly 12 and shield assembly 16 and holds shield assembly 16 in the collapsed condition of FIG. 2.

Passively activated safety needle assembly 10 is shown in FIG. 1 after removal from its sterile packaging and prior to mounting on a medical implement. Safety needle assembly 10 is mounted to needle holder 18 or other medical implement by urging your receptacle 36 at proximal end 34 of needle holder 30 onto Luer tip 20 as shown in FIG. 2. The health care worker then grips needle holder 18 and distal arm 42 of shield assembly 16 with a thumb and forefinger and pulls distally on safety cap 14 with the other hand. A slight pulling force separates safety cap 14 from the remainder of needle assembly 10 to expose distal end 26 of needle cannula 22. At this point, the health care worker still retains a finger on distal arm 42 of shield assembly 16 to hold safety shield 38 in the proximal position shown in FIG. 2.

Figure 3:
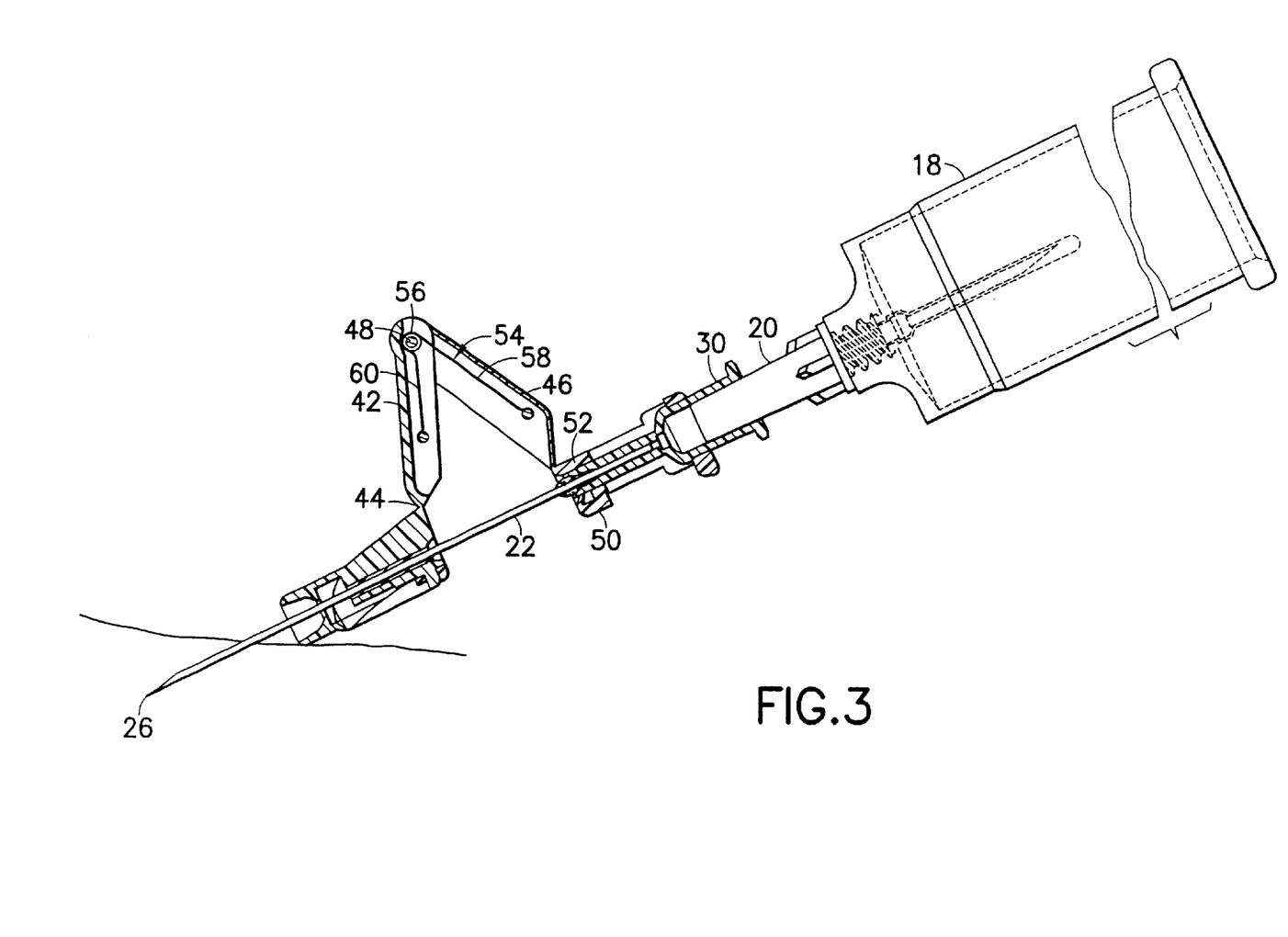
FIG. 3 is a cross-sectional view similar to FIG. 2, but showing the safety cap removed and showing the needle assembly in use.

The health care worker next guides the distal end 26 of needle cannula 22 into a targeted location on a patient substantially in the conventional manner. The health care worker may release the grip on distal arm 42 of shield assembly 16 once there is assurance that the targeted location of the patient has been entered. The removal of the digital force enables torsion spring 54 to expand, and immediately urges safety shield 38 distally along needle cannula 22. Safety shield 38 will terminate its distal movement upon contact with the skin of the patient as shown in FIG. 3.

Needle assembly 12 is removed from the patient after a sufficient volume of fluid has been collected or delivered. Removal of needle cannula from the patient merely involves a proximal movement of passively activated safety needle assembly 10 and needle holder 18. This proximal movement permits further distal movement of safety shield 38 along needle cannula 22 in response to continuing forces exerted by torsion spring 54. Upon complete removal of needle cannula 22 from the patient, safety shield 38 will have been propelled distally a sufficient distance for latch 40 to spring over distal tip 26 of needle cannula 20 and to prevent re-exposure of needle cannula 22. Sliding movement of safety shield 38 along needle cannula 22 is entirely passive and requires no initial assistance by the health care worker. Needle assembly 12 then can be discarded with or without the holder 18 in an appropriate sharps receptacle.

Figure 5:
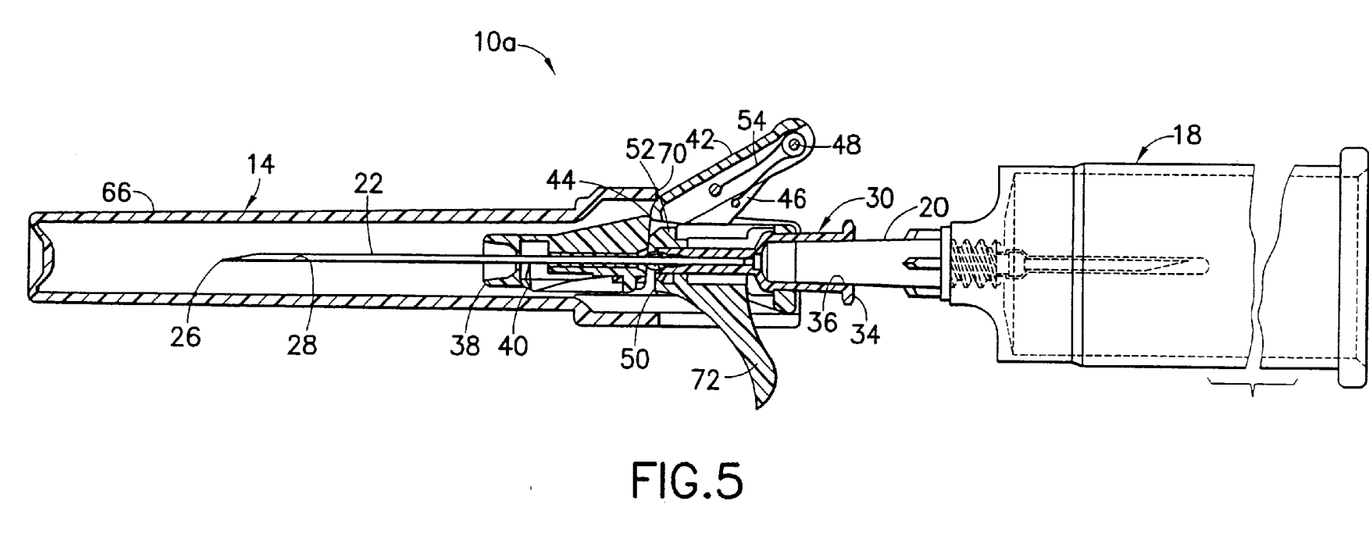
FIG. 5 is a cross-sectional view similar to FIG. 2, but showing the second embodiment.

A second embodiment of the passively activated safety needle assembly is illustrated in FIG. 5 and is identified generally by the numeral 10a. Passively activated safety needle assembly 10a is identical to safety needle assembly 10 described and illustrated above in most respects. However, a rigid thumb grip 72 projects from a side of base 50 diametrically opposite arms 44 and 46. Safety cap 14a includes a second notch 74 diametrically opposite notch 68 and dimensioned to slidably receive thumb grip 72. Thumb grip 72 provides a convenient gripping location that is similar to grips provided on many needle sets used for fluid specimen collection purposes.

The health care technician can use passively activated safety needle assembly 10a substantially as described above, but will grip both distal arm 42 and thumb grip 72 during removal of safety cap 14 and during initial insertion of needle cannula 22 into the patient. The health care worker then can release the finger grip on the distal arm 42, thereby permitting torsion spring 54 to propel safety shield 38 distally along needle cannula 22, as described above.

Figure 6:
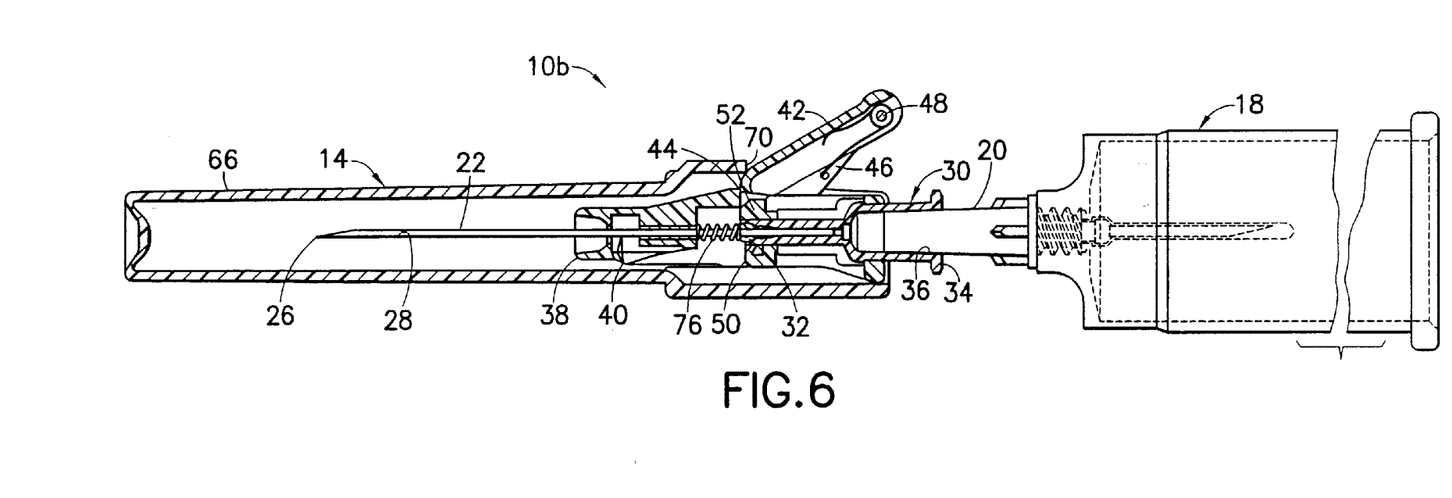
FIG. 6 is a cross-sectional view similar to FIGS. 2 and 5 but showing a third embodiment.

A third embodiment of the passively shieldable safety needle assembly is identified by the numeral 10b by FIG. 6. Passively activated safety needle assembly 10b is identical to safety needle assembly 10 of FIGS. 1–4 in most respects. However, passively activated safety needle assembly 10b has a coil spring 76 mounted around needle cannula 22 and disposed between needle hub 30 and safety shield 38. Coil spring 76 replaces torsion spring 54 of the first embodiment, and works with a similar result. However coil spring 76 exerts biasing forces directly on safety shield 38. As a result, arm 42 and 46 of shield assembly 16 merely follow safety shield 38 rather than driving safety shield 38. Arms 42 and 46 continue to perform their function of limiting the amount of distal movement of safety shield 38 along needle cannula 22.

Figure 7:
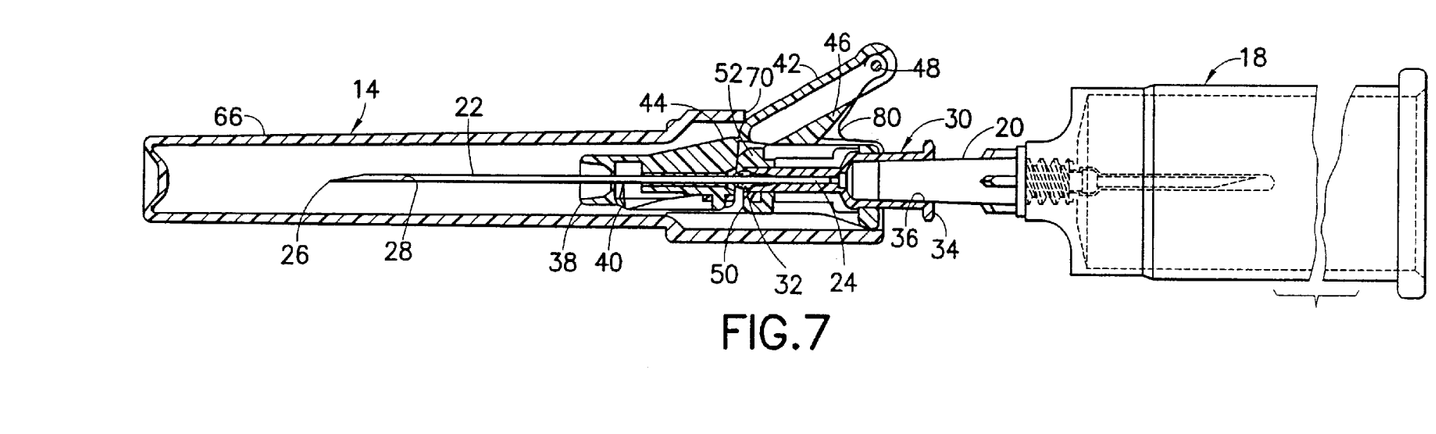
FIG. 7 is a cross-sectional view similar to FIGS. 2, 5 and 6 but showing a fourth embodiment.

A fourth embodiment of the passively activated safety needle assembly of the subject invention is identified by the numeral 10c in FIG. 7. Passively activated safety needle assembly 10c is substantially identical to passively activated safety needle assembly 10 of FIGS. 1–5 in virtually all respects. However, a torsion spring 80 is provided between base 50 of shield assembly 16 and proximal arm 46. Torsion spring 80 rotatably drives proximal arm 58 about second living hinge 52. This rotation of proximal arm 46 causes a corresponding rotational movement of distal arm 42 and drives safety shield 38 distally along needle cannula 22 substantially as described above.

What is claimed is:

1. A passively activated safety needle assembly comprising:
   a needle cannula with opposite proximal and distal ends; and
   a shield assembly having a safety shield slidably mounted on said needle cannula and movable from a proximal position substantially adjacent said proximal end of said needle cannula to a distal position surrounding said distal end of said needle cannula, said shield assembly further comprising a plurality of hingedly connected arms with at least two arms being hingedly connected at a hinge connection extending between said safety shield and a location in proximity to said proximal end of said needle cannula for limiting distal movement of said safety shield along said needle cannula, said shield assembly further comprising a torsion spring securably disposed at said hinge connection for urging said safety shield from said proximal position to said distal position.

2. The passively activated safety needle assembly of claim 1, further comprising a safety cap frictionally mounted over said needle cannula ond over portions of said shield assembly for holding said safety shield in said proximal position.

3. The passively activated safety needle assembly of claim 1, further comprising a needle hub secured to said proximal end of said needle cannula, and wherein said plurality of arms comprises a distal arm articulated to said safety shield and a proximal arm articulated in proximity to said hub, said proximal and distal arms being hingedly connected to one another at said hinge connection.

4. The passively activated safety needle assembly of claim 3, wherein said torsion spring is disposed between said hub and said proximal arm, said torsion spring urging said proximal arm about said articulation to said base for expanding said proximal and distal arms relative to one another and propelling said safety shield distally along said needle cannula.

5. The passively activated safety needle assembly of claim 4, wherein the base further comprises a thumb grip projecting from said base at a location opposite said proximal arm.

6. The passively activated safety needle assembly of claim 3, wherein said torsion spring is mounted at said hinged connection between said proximal and distal arms for urging said proximal and distal arms into an expanded condition and thereby driving said safety shield distally along said needle cannula.

7. The passively activated safety needle assembly of claim 3, wherein said shield assembly further comprises a base securely mounted to said needle hub, said proximal arm being articulated to said base.

8. The passively activated safety needle assembly of claim 3, wherein said safety cap includes a notch for slidably receiving said arms and holding said arms in a collapsed condition.

9. The passively activated safety needle assembly of claim 3, wherein said safety shield is unitary with said distal arm.

10. The passively activated safety needle assembly of claim 3, wherein said proximal arm is unitary with said base.

11. A passively activated safety needle assembly comprising:
    a needle assembly having a needle cannula with opposite proximal and distal ends, a needle hub securely mounted to said proximal end of said needle cannula and being configured for mounting to a medical implement;
    a shield assembly having a safety shield slidably mounted on said needle cannula and movable from a proximal position adjacent said hub to a distal position surrounding said distal end of said needle cannula, said shield assembly further comprising a distal arm hingedly connected to said safety shield, a proximal arm hingedly connected to said distal arm at a hinge and a base hingedly connected to said proximal arm, said base being securely mounted to said hub of said needle assembly, said shield assembly further comprising a torsion spring secured to said hinge and mounted to at least one of said arms for moving said arms in a direction for urging said safety shield to said distal position; and
    a safety cap releasably engaged over said needle cannula and over portions of said shield assembly for holding said shield assembly in said proximal position.

\* \* \* \* \*